(12) United States Patent
Chouinard et al.

(10) Patent No.: US 11,975,182 B2
(45) Date of Patent: May 7, 2024

(54) CIRCULATORY SUPPORT DEVICE WITH INTEGRATED CANNULA

(71) Applicant: Boston Scientific Scimed Inc, Maple Grove, MN (US)

(72) Inventors: Paul F. Chouinard, Maple Grove, MN (US); Thomas P. Jancaric, Maple Grove, MN (US); David B. Robinson, Independence, MN (US); Gerasimos Rigalos, County Galway (IE); James Tormey, Oranmore (IE)

(73) Assignee: Boston Scientific Scimed, Inc., Maple Grove, MN (US)

( * ) Notice: Subject to any disclaimer, the term of this patent is extended or adjusted under 35 U.S.C. 154(b) by 553 days.

(21) Appl. No.: 17/012,006

(22) Filed: Sep. 3, 2020

(65) Prior Publication Data
US 2021/0069397 A1    Mar. 11, 2021

Related U.S. Application Data

(60) Provisional application No. 62/896,379, filed on Sep. 5, 2019.

(51) Int. Cl.
*A61M 60/855*    (2021.01)
*A61M 1/36*    (2006.01)
(Continued)

(52) U.S. Cl.
CPC ........ *A61M 60/148* (2021.01); *A61M 1/3659* (2014.02); *A61M 39/10* (2013.01);
(Continued)

(58) Field of Classification Search
CPC .. A61M 2025/0024; A61M 2025/0681; A61M 25/0012; A61M 1/3659
See application file for complete search history.

(56) References Cited

U.S. PATENT DOCUMENTS

2007/0203391 A1*   8/2007   Bloom ............. A61B 17/00234
                                                            606/151
2008/0086027 A1    4/2008   Siess et al.
(Continued)

FOREIGN PATENT DOCUMENTS

GB    2504175 A    1/2014
JP    2017-140474 A    8/2017
(Continued)

OTHER PUBLICATIONS

International Search Report and Written Opinion for PCT/US2020/049286, filed Sep. 3, 2020, dated Dec. 15, 2020.

*Primary Examiner* — Michael J D'Abreu
(74) *Attorney, Agent, or Firm* — Seager, Tufte & Wickhem LLP

(57) ABSTRACT

Embodiments of the present disclosure relate to a circulatory support device with an integrated cannula. In an exemplary embodiment, an apparatus for attachment to a cardiac pump, comprises an adaptor. The adaptor comprises an annular cross section configured to receive the cardiac pump. The annular cross section is secured to the cardiac pump. The adaptor also comprises a plurality of channels arranged around the adapter and a cannula comprising a proximal portion, a distal portion, and an intermediate portion comprising a braided mesh extending between the distal portion and the proximal portion. The proximal portion has a proximal end comprising a plurality of elements arranged through the channels and the distal portion comprises a plurality of wires and a tip element. The plurality of wires extend in a distal direction from the braided mesh to the tip element and are secured to the tip element. And, a coating covers at least a portion of the braided mesh.

16 Claims, 10 Drawing Sheets

(51) Int. Cl.
*A61M 39/10* (2006.01)
*A61M 60/148* (2021.01)
*A61M 60/857* (2021.01)

(52) U.S. Cl.
CPC ... *A61M 60/857* (2021.01); *A61M 2039/1077* (2013.01); *A61M 2210/125* (2013.01)

(56) References Cited

U.S. PATENT DOCUMENTS

| | | |
|---|---|---|
| 2011/0004046 A1 | 1/2011 | Campbell et al. |
| 2012/0172655 A1 | 7/2012 | Campbell |
| 2013/0053623 A1 | 2/2013 | Evans |
| 2014/0012065 A1 | 1/2014 | Fitzgerald |
| 2019/0070345 A1 | 3/2019 | McBride |

FOREIGN PATENT DOCUMENTS

| | | | |
|---|---|---|---|
| WO | 2017/159849 A1 | 9/2017 | |
| WO | 2018089970 A1 | 5/2018 | |
| WO | 2018226991 A1 | 12/2018 | |
| WO | WO-2019229211 A1 * | 12/2019 | .......... A61M 60/135 |

* cited by examiner

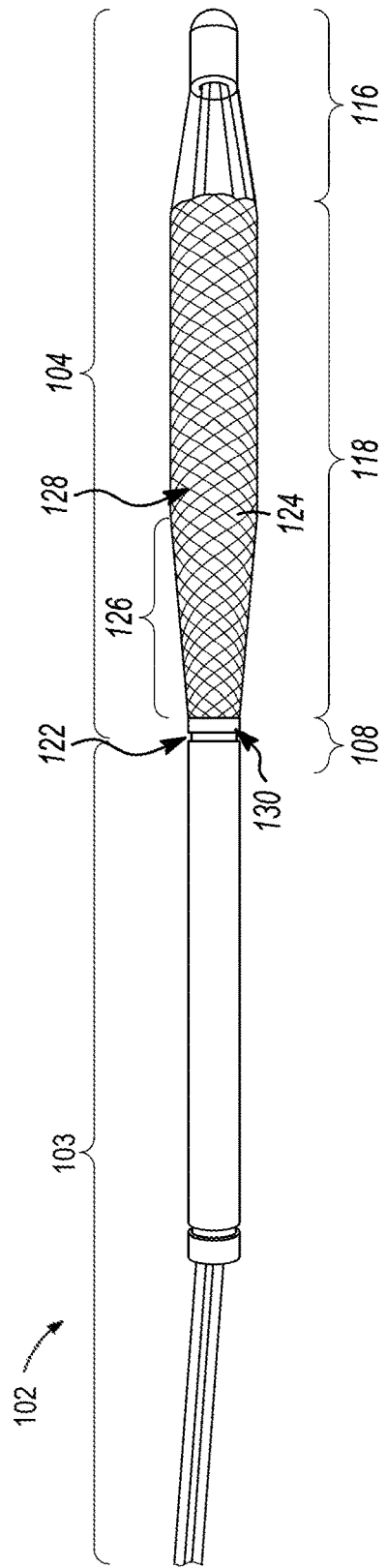
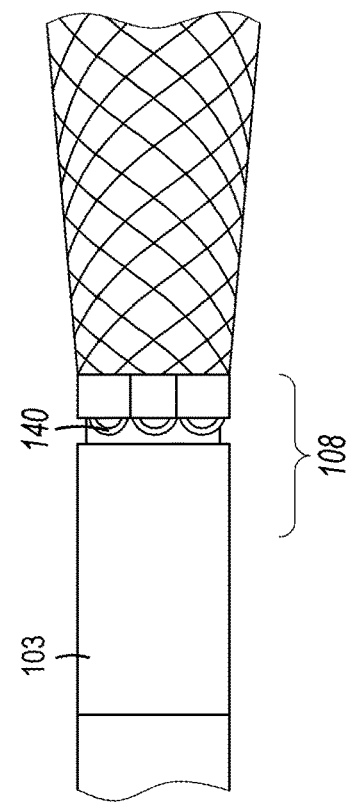
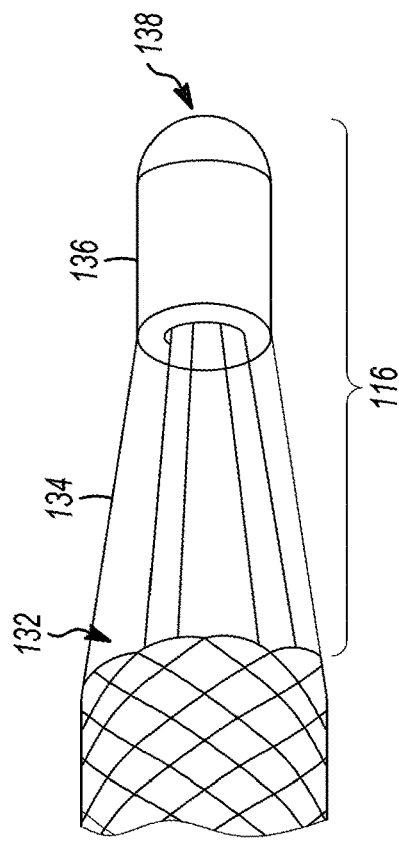
FIG. 2
FIG. 3
FIG. 4

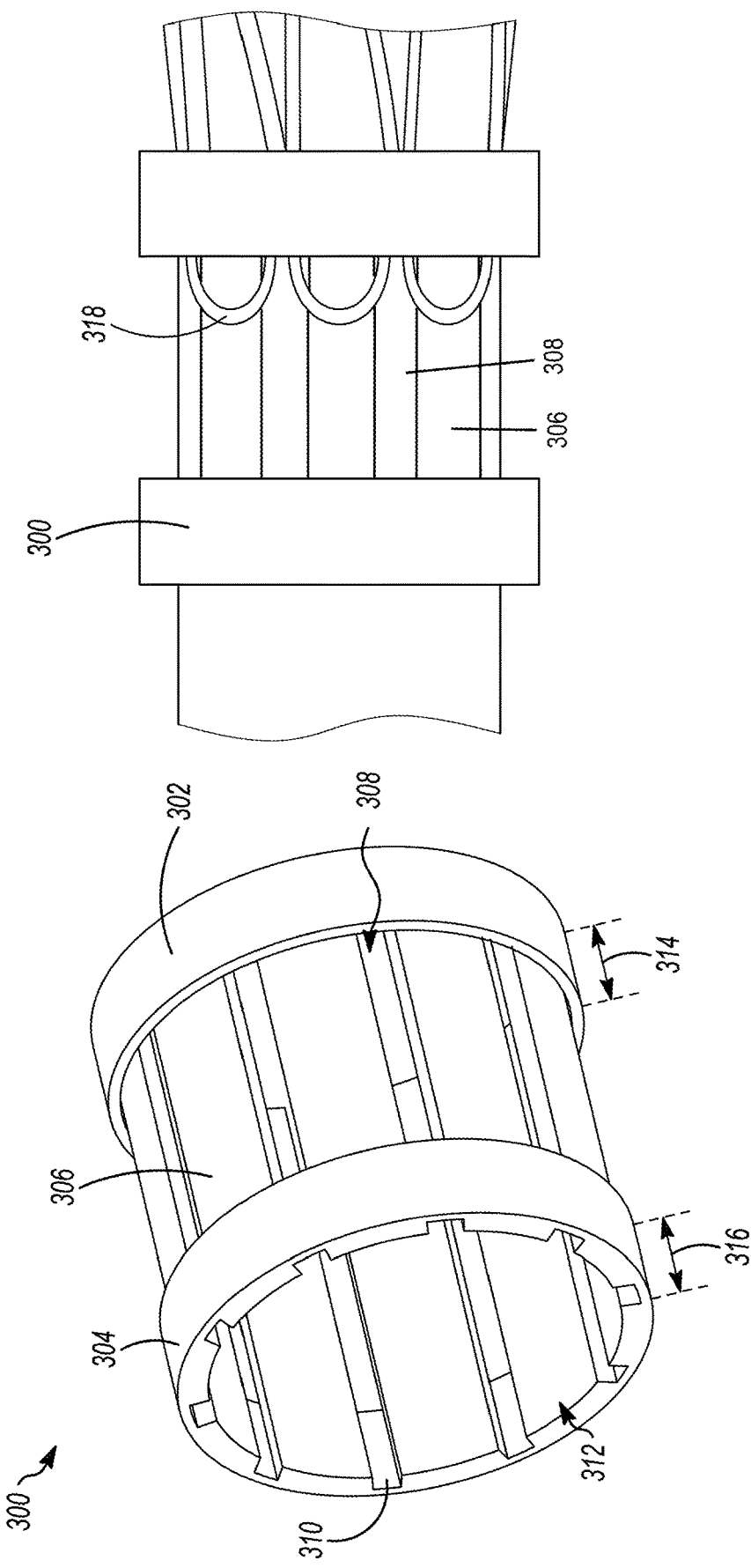

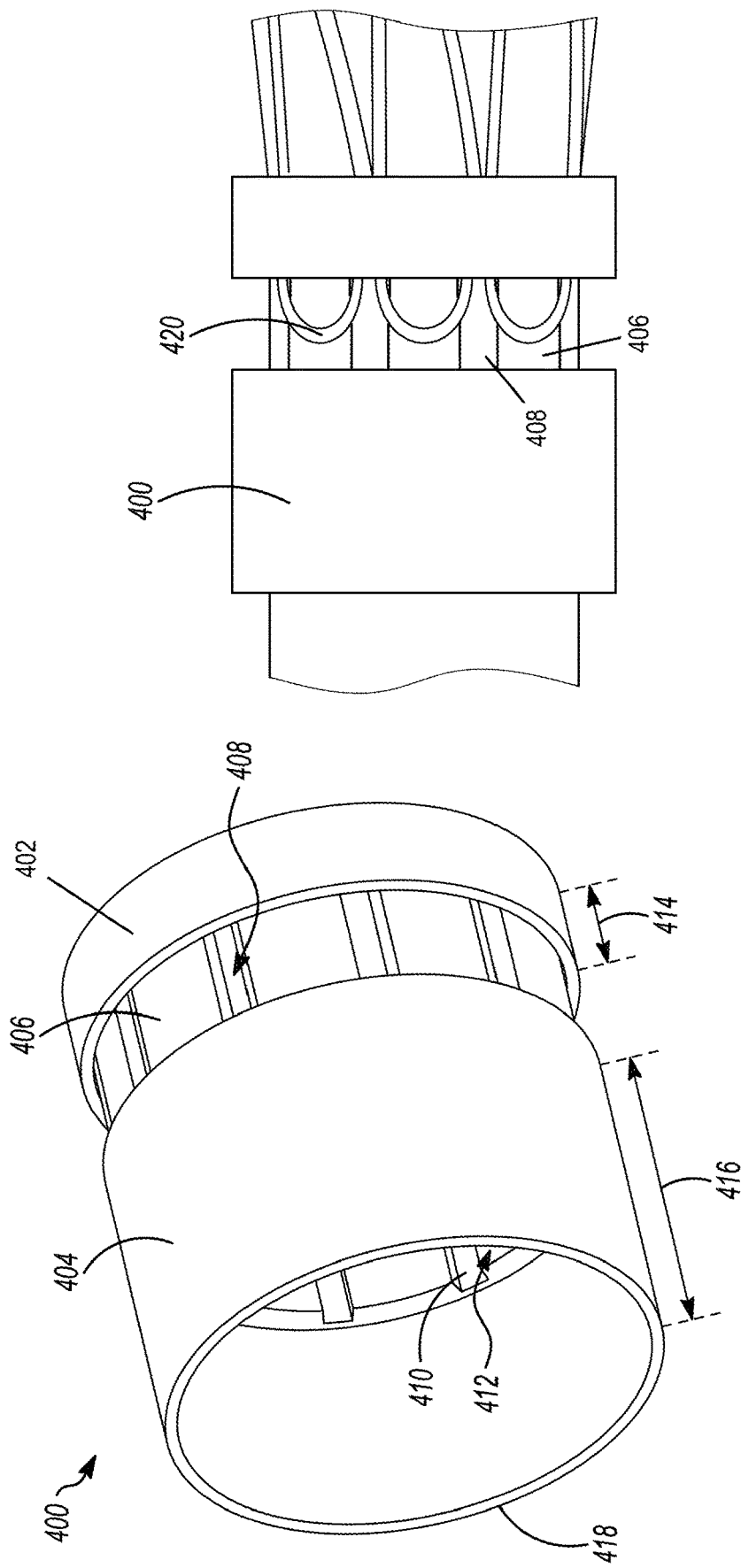

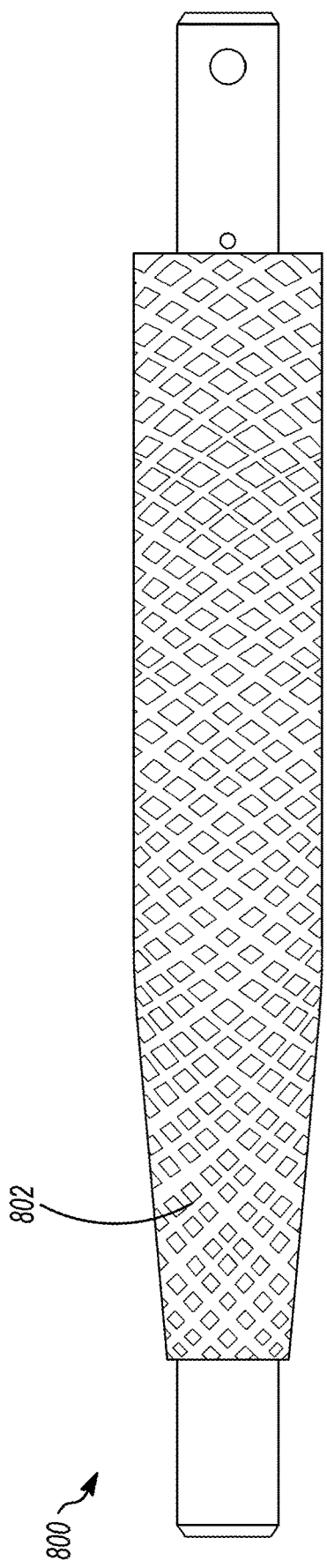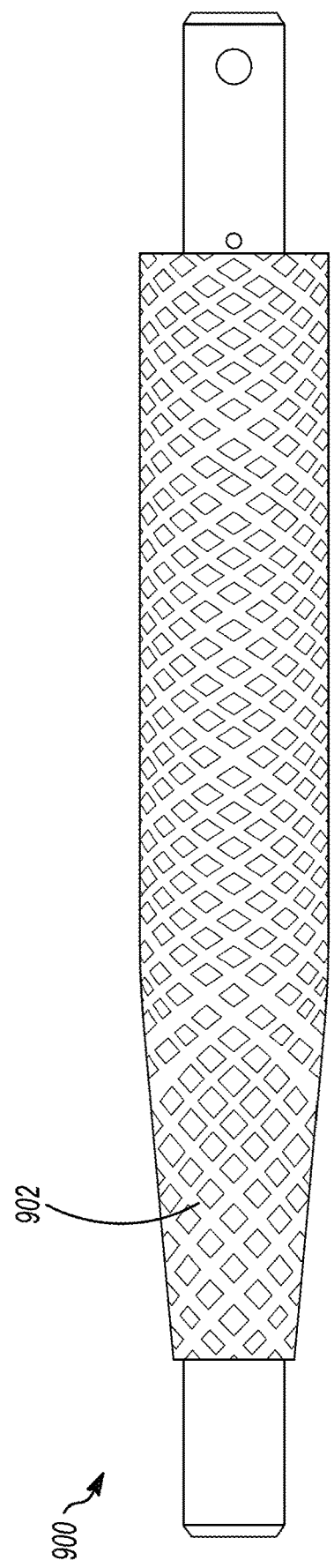

CIRCULATORY SUPPORT DEVICE WITH INTEGRATED CANNULA

CROSS REFERENCE TO RELATED APPLICATION

This application claims priority to Provisional Application No. 62/896,379, filed Sep. 5, 2019, which is herein incorporated by reference in its entirety.

TECHNICAL FIELD

The present disclosure relates to percutaneous circulatory support devices. More specifically, the disclosure relates to integrated braided cannulas for a circulatory support pump.

BACKGROUND

Circulatory support devices support the pumping action of the heart. These devices may be disposed through a valve opening such as, for example, an aortic valve. Blood flow through the circulatory support devices is an important factor when differentiating between different types of circulatory support devices.

SUMMARY

Embodiments disclosed herein relate to circulatory support devices that have an increased flow capability in comparison to conventional embodiments. Exemplary embodiments include, but are not limited to, the following examples.

In an Example 1, an apparatus for attachment to a cardiac pump, the apparatus comprises: an adaptor comprising: an annular cross section configured to receive the cardiac pump, wherein the annular cross section is secured to the cardiac pump; and a plurality of channels arranged around the adapter; a cannula comprising a proximal portion, a distal portion, and an intermediate portion comprising a braided mesh extending between the distal portion and the proximal portion, the proximal portion having a proximal end comprising a plurality of elements arranged through the channels and the distal portion comprising a plurality of wires and a tip element, wherein the plurality of wires extend in a distal direction from the braided mesh to the tip element, wherein the plurality of wires are secured to the tip element; and a coating covering at least a portion of the braided mesh.

In an Example 2, the apparatus of Example 1, wherein a proximal portion of the braided mesh comprises a tapered portion that increases in diameter from a proximal end of the tapered portion to a distal end of the tapered portion.

In an Example 3, the apparatus of any one of Examples 1 or 2, wherein the braided mesh comprises a constant pitch.

In an Example 4, the apparatus of any one of Examples 1 or 2, wherein the braided mesh comprises a varying pitch.

In an Example 5, the apparatus of any one of Examples 1-3, wherein the channels extend along an interior surface of the adaptor.

In an Example 6, the apparatus of Example 5, wherein the channels extend along an entire length of the adaptor.

In an Example 7, the apparatus of any one of Examples 1-6, wherein the adaptor comprises a distal cylindrical portion, a proximal cylindrical portion, and a plurality of elongate members extending from the distal cylindrical portion to the proximal cylindrical portion, wherein conduits extending through a thickness of the adaptor separate each of the elongate members.

In an Example 8, the apparatus of any one of Examples 1-7, wherein at least one of the plurality of channels extends longitudinally.

In an Example 9, the apparatus of any one of Examples 1-8, wherein the adaptor comprises a distal cylindrical portion, a proximal cylindrical portion, and one or more intermediate cylindrical portions extending between the distal cylindrical portion and the proximal cylindrical portion, wherein the intermediate cylindrical portion has a smaller diameter than the distal cylindrical portion, and wherein the channels extend through a length of the distal cylindrical portion.

In an Example 10, the apparatus of any one of Examples 1-9, wherein the plurality of elements arranged through the channels are a plurality of loop elements.

In an Example 11, a method for manufacturing an apparatus for attachment to a cardiac pump, the method comprises: arranging proximal ends of a plurality of wires through a plurality of channels of an adaptor; braiding an intermediate portion of the plurality of wires to create a braided mesh; extending a distal portion of the plurality of wires in a distal direction; coating at least a portion of the braided mesh; and coupling a distal end of the distal portion to a tip element.

In an Example 12, the method of Example 11, wherein the braided mesh comprises a constant pitch.

In an Example 13, the method of Example 11, wherein the braided mesh comprises a varying pitch.

In an Example 14, the method of any one of Examples 11-13, wherein the adaptor comprises a distal cylindrical portion, a proximal cylindrical portion, and a plurality of elongate members extending from the distal cylindrical portion to the proximal cylindrical portion, wherein conduits extending through a thickness of the adaptor separate each of the elongate members, and wherein arranging proximal ends of the plurality of wires through the plurality of channels comprises arranging the proximal ends through the conduits.

In an Example 15, the method of any one of Examples 11-13, wherein the adaptor comprises a distal cylindrical portion, a proximal cylindrical portion, and one or more intermediate cylindrical portions extending between the distal cylindrical portion and the proximal cylindrical portion, wherein the intermediate cylindrical portion has a smaller diameter than the distal cylindrical portion, wherein the channels extend through a length of the distal cylindrical portion, and wherein arranging proximal ends of the plurality of wires through the plurality of channels comprises arranging the proximal ends through the channels.

In an Example 16, an apparatus for attachment to a cardiac pump, the apparatus comprises: an adaptor comprising: an annular cross section configured to receive the cardiac pump, wherein the annular cross section is secured to the cardiac pump; and a plurality of channels arranged around the adapter; a cannula comprising a proximal portion, a distal portion, and an intermediate portion comprising a braided mesh extending between the distal portion and the proximal portion, the proximal portion having a proximal end comprising a plurality of elements arranged through the channels and the distal portion comprising a plurality of wires and a tip element, wherein the plurality of wires extend in a distal direction from the braided mesh to the tip element, wherein the plurality of wires are secured to the tip element; and a coating covering at least a portion of the braided mesh.

In an Example 17, the apparatus of Example 16, wherein a proximal portion of the braided mesh comprises a tapered portion that increases in diameter from a proximal end of the tapered portion to a distal end of the tapered portion.

In an Example 18, the apparatus of Example 16, wherein the braided mesh comprises a constant pitch.

In an Example 19, the apparatus of Example 16, wherein the braided mesh comprises a varying pitch.

In an Example 20, the apparatus of Example 16, wherein the channels extend along an interior surface of the adaptor.

In an Example 21, the apparatus of Example 20, wherein the channels extend along an entire length of the adaptor.

In an Example 22, the apparatus of Example 16, wherein at least one of the plurality of channels extends longitudinally.

In an Example 23, the apparatus of Example 16, wherein the adaptor comprises a distal cylindrical portion, a proximal cylindrical portion, and a plurality of elongate members extending from the distal cylindrical portion to the proximal cylindrical portion, wherein conduits extending through a thickness of the adaptor separate each of the elongate members.

In an Example 24, the apparatus of Example 23, wherein the elongate members extend along an interior surface of the distal cylindrical portion, the proximal cylindrical portion, or both.

In an Example 25, the apparatus of Example 24, wherein the elongate members extend along an entire length of the distal cylindrical portion, the proximal cylindrical portion, or both.

In an Example 26, the apparatus of Example 16, wherein the adaptor comprises a distal cylindrical portion, a proximal cylindrical portion, and one or more intermediate cylindrical portions extending between the distal cylindrical portion and the proximal cylindrical portion, wherein the intermediate cylindrical portion has a smaller diameter than the distal cylindrical portion, and wherein the channels extend through a length of the distal cylindrical portion.

In an Example 27, the apparatus of Example 16, wherein the plurality of elements are a plurality of loop elements.

In an Example 28, a method for manufacturing an apparatus, the method comprises: arranging proximal ends of a plurality of wires through a plurality of channels of an adaptor; braiding an intermediate portion of the plurality of wires to create a braided mesh; extending a distal portion of the plurality of wires in a distal direction; coating at least a portion of the braided mesh; and coupling a distal end of the distal portion to a tip element.

In an Example 29, the method of Example 28, wherein braiding the intermediate portion comprises forming a tapered portion that increase in diameter from a proximal end of the tapered portion to a distal end of the tapered portion.

In an Example 30, the method of Example 28, wherein the braided mesh comprises a constant pitch.

In an Example 31, the method of Example 28, wherein the braided mesh comprises a varying pitch.

In an Example 32, the method of Example 28, wherein the adaptor comprises a distal cylindrical portion, a proximal cylindrical portion, and a plurality of elongate members extending from the distal cylindrical portion to the proximal cylindrical portion, wherein conduits extending through a thickness of the adaptor separate each of the elongate members, and wherein arranging proximal ends of the plurality of wires through the plurality of channels comprises arranging the proximal ends through the conduits.

In an Example 33, the method of Example 28, wherein the adaptor comprises a distal cylindrical portion, a proximal cylindrical portion, and one or more intermediate cylindrical portions extending between the distal cylindrical portion and the proximal cylindrical portion, wherein the intermediate cylindrical portion has a smaller diameter than the distal cylindrical portion, wherein the channels extend through a length of the distal cylindrical portion, and wherein arranging proximal ends of the plurality of wires through the plurality of channels comprises arranging the proximal ends through the channels.

In an Example 34, the method of Example 28, further comprising attaching the adaptor to the cardiac pump.

In an Example 35, the method of Example 28, wherein the coating is silicone.

While multiple embodiments are disclosed, still other embodiments of the presently disclosed subject matter will become apparent to those skilled in the art from the following detailed description, which shows and describes illustrative embodiments of the disclosed subject matter. Accordingly, the drawings and detailed description are to be regarded as illustrative in nature and not restrictive.

BRIEF DESCRIPTION OF THE DRAWINGS

FIG. 2 depicts a side view of the circulatory support device 102 depicted in FIG. 1 including a pump 103, in accordance with embodiments of the subject matter disclosed herein FIG. 3 depicts a side view of a distal portion of the cannula depicted in FIG. 2, in accordance with embodiments of the subject matter disclosed herein.

FIG. 4 depicts a side view of a proximal portion of the cannula and adaptor depicted in FIG. 2, in accordance with embodiments of the subject matter disclosed herein.

FIG. 6A depicts a perspective view of another exemplary adaptor and FIG. 6B depicts a side view of the exemplary adaptor including wire elements coupled thereto, in accordance with embodiments of the subject matter disclosed herein.

FIG. 7A depicts a perspective view of even another exemplary adaptor and FIG. 7B depicts a side view of the exemplary adaptor including wire loops, in accordance with embodiments of the subject matter disclosed herein.

FIG. 12 depicts is a side view of another exemplary mandrel used to form an exemplary cannula, in accordance with embodiments of the subject matter disclosed herein.

FIG. 13 depicts is a side view of even another exemplary mandrel used to form an exemplary cannula, in accordance with embodiments of the subject matter disclosed herein.

Figure 1:
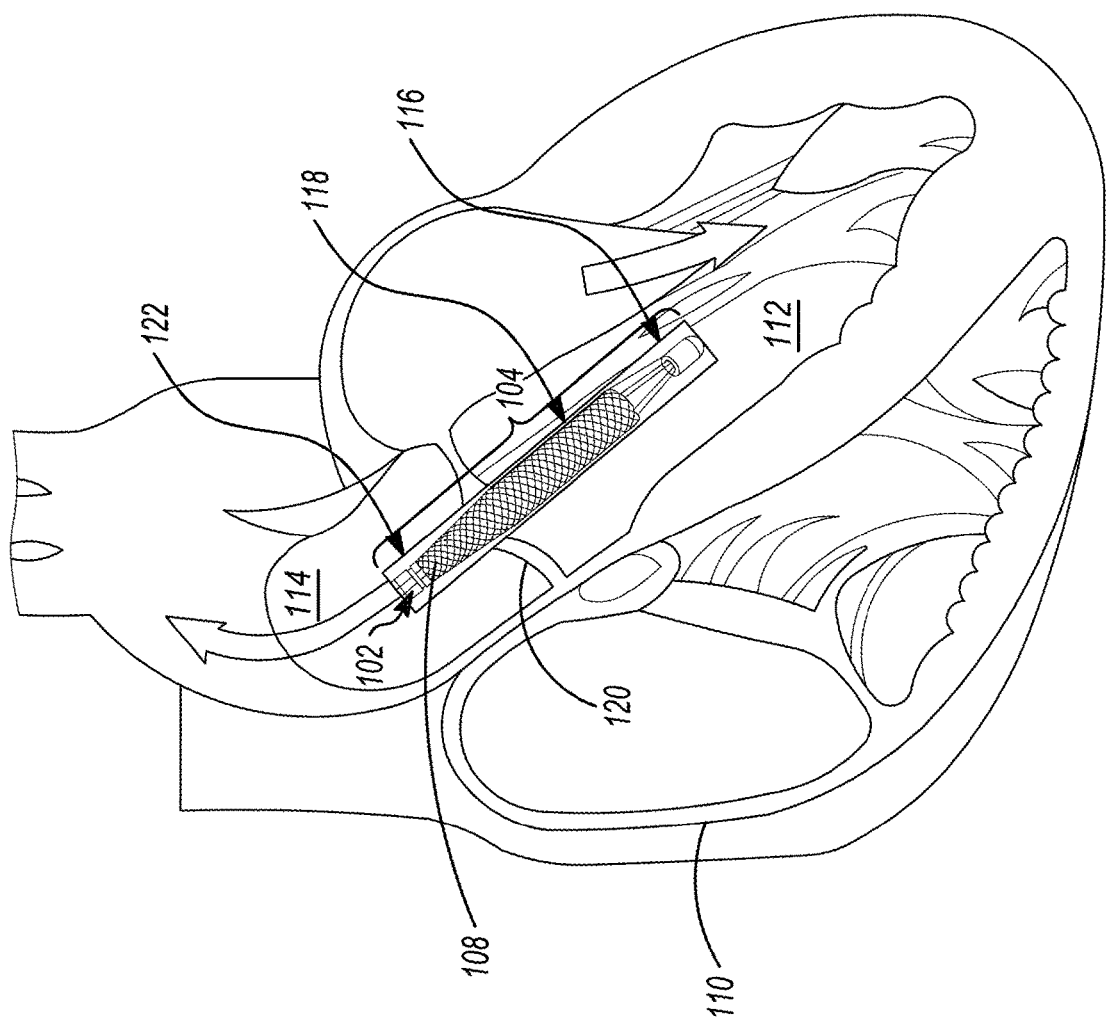
FIG. 1 depicts a conceptual diagram of a circulatory support device including a cannula and an adaptor, in accordance with embodiments of the subject matter disclosed herein.

While the disclosed subject matter is amenable to various modifications and alternative forms, specific embodiments have been shown by way of example in the drawings and are described in detail below. The intention, however, is not to limit the subject matter disclosed herein to the particular embodiments described. On the contrary, the disclosure is intended to cover all modifications, equivalents, and alternatives falling within the scope of the subject matter disclosed herein, and as defined by the appended claims.

DETAILED DESCRIPTION

Embodiments disclosed herein include circulatory support devices that have an increased flow capability in comparison to conventional embodiments.

FIG. 1 depicts a conceptual diagram of a circulatory support device 102 including a cannula 104 and an adaptor 108, in accordance with embodiments of the subject matter disclosed herein. The circulatory support device 102 is shown arranged within a heart 110. According to embodiments, the circulatory support device 102 may include a ventricular assist device (shown in FIG. 2), such as a pump, that is coupled to the cannula 104 by the adaptor 108. The ventricular assist device is configured to pump blood from the subject's left ventricle 112 into the subject's aorta 114. In embodiments, the circulatory support device 102 may be used to treat cardiogenic shock and other heart failure modalities.

In embodiments, a distal portion 116 of the circulatory support device 102 is arranged in the left ventricle 112. An intermediate portion 118 of the circulatory support device 102 extends through the aortic valve 120 so that a proximal portion 122 of the cannula 104 extends into the aorta 114. In embodiments, the proximal portion 122 of the cannula 104 is coupled to the adaptor 108 and the adaptor 108 is coupled to the circulatory support device 102. During operation, the circulatory support device 102 draws blood from the left ventricle 112, through the cannula 104 of the circulatory support device 102 and is released into the aorta 114. Additionally, or alternatively, the circulatory support device 102 may be used to facilitate pumping blood from some other aspect of the subject's vasculature into an adjacent portion of the vasculature.

FIG. 1 is not intended to suggest any limitation as to the scope of use or functionality of embodiments of the present disclosure. FIG. 1 also should not be interpreted as having any dependency or requirement related to any single component or combination of components illustrated therein. Additionally, various components depicted in FIG. 1 may be, in embodiments, integrated with various ones of the other components depicted therein (and/or components not illustrated), all of which are considered to be within the ambit of the present disclosure.

FIG. 2 depicts a side view of the circulatory support device 102 depicted in FIG. 1 including the ventricular assist device 103, in accordance with embodiments of the subject matter disclosed herein.

As stated above, the cannula 104 may include a proximal portion 122, an intermediate portion 118, and a distal portion 116. The intermediate portion 118 may include a braided mesh 124 that extends between the proximal portion 122 and the distal portion 116. In embodiments, the braided mesh 124 may have various braid angles and/or varying braid angles, as explained in more detail below. In embodiments, a proximal portion 126 of the braided mesh 124 may be tapered. The tapered proximal portion 126 may transition the braided mesh 124 from a larger diameter (e.g., greater than or equal to 5 millimeters (mm)) near a distal end 128 of the proximal portion 126 to a smaller diameter near a proximal end 130 of the braided mesh 124. In embodiments, the braided mesh 124 may be collapsed into a smaller diameter for delivery into the heart 110. Once arranged within the heart 110, the braided mesh 124 may be expanded to its larger diameter. By being able to expand to a larger diameter than its delivery configuration, the cannula 104 may provide larger flow rates than can be provided with a non-expandable smaller diameter cannula. In embodiments, the braided mesh 124 may be designed to adequately withstand the pressure gradient between the inside and the outside of the cannula 104.

In embodiments, the braided mesh 124 is coated with a membrane to form a conduit through the cannula 104 from the distal portion 116 to the proximal portion 122. In embodiments, the membrane may be silicone. In embodiments, the cannula 104 is formed from a plurality of nitinol wires having a diameter of 0.008". However, this is only an example and other types of wires having other diameters may be used to form the cannula 104. Additionally, or alternatively, wires having varying diameters may be used to form the cannula 104. In embodiments, the cannula 104 may be formed from a range of nitinol wires (e.g., 6 wires to 48 wires).

FIG. 2 is not intended to suggest any limitation as to the scope of use or functionality of embodiments of the present disclosure. FIG. 2 also should not be interpreted as having any dependency or requirement related to any single component or combination of components illustrated therein. Additionally, various components depicted in FIG. 2 may be, in embodiments, integrated with various ones of the other components depicted therein (and/or components not illustrated), all of which are considered to be within the ambit of the present disclosure.

FIG. 3 depicts a side view of a distal portion 116 of the cannula 104 depicted in FIG. 2, in accordance with embodiments of the subject matter disclosed herein. In embodiments, at the distal end 132 of the braided mesh 124, the wires of the cannula 104 may include wires 134 that extend in a distal direction and be coupled to a tip element 136. The spaces between the wires 134 provide an inlet for blood to enter the cannula 104. Additionally, or alternatively, the tip element 136 may prevent the suction of tissue into the cannula 104. Additionally, or alternatively, the tip element 136 may be radiopaque to help determine proper positioning of the cannula 104. In embodiments, the tip element 136 may include an opening at its distal end 138 so a guidewire can be passed through the opening to guide the cannula 104 to an appropriate location within the heart 110.

FIG. 3 is not intended to suggest any limitation as to the scope of use or functionality of embodiments of the present disclosure. FIG. 3 also should not be interpreted as having any dependency or requirement related to any single component or combination of components illustrated therein. Additionally, various components depicted in FIG. 3 may be, in embodiments, integrated with various ones of the other components depicted therein (and/or components not illustrated), all of which are considered to be within the ambit of the present disclosure.

FIG. 4 depicts a side view of a proximal portion 122 of the cannula 104 and the adaptor 108 depicted in FIG. 2, in accordance with embodiments of the subject matter disclosed herein. In embodiments, the proximal portion 122 of the cannula 104 may have an annular cross section and is coupled to the adaptor 108. For example, the braided mesh 124 may include a plurality of wire elements 140 that are arranged through channels in the adaptor 108 to interlock the wires of the cannula 104 to the adaptor 108, as described in more detail below. In embodiments, the plurality of wire elements 140 may be a plurality of wire loop elements. In embodiments, any of the wire loop elements discussed herein may be replaced with linear elements and/or other wire elements. For example, the wire elements 140 may be linear elements that are arranged through the channels of the adaptor 124 and secured to the adaptor 108 by an interference fit between the adaptor 108 and the proximal portion 122 of the cannula 104. In embodiments, the elements 140 may be welded to the adaptor 108 and/or secure to the adaptor in another manner using, for example, an adhesive, etc. The wire elements 140 facilitate attaching the braided mesh 124 to the adaptor 108 while maintaining a small cross-sectional profile for the proximal portion 122 of the cannula 104.

In embodiments, the adaptor 108 may also be coupled to a ventricular assist device 103, which facilitates the flow of blood through the cannula 104. In embodiments, the adaptor 108 be coupled to the ventricular assist device 103 by welding, soldering, screw fitting, and/or the like.

FIG. 4 is not intended to suggest any limitation as to the scope of use or functionality of embodiments of the present disclosure. FIG. 4 also should not be interpreted as having any dependency or requirement related to any single component or combination of components illustrated therein. Additionally, various components depicted in FIG. 4 may be, in embodiments, integrated with various ones of the other components depicted therein (and/or components not illustrated), all of which are considered to be within the ambit of the present disclosure.

Figure 5B:
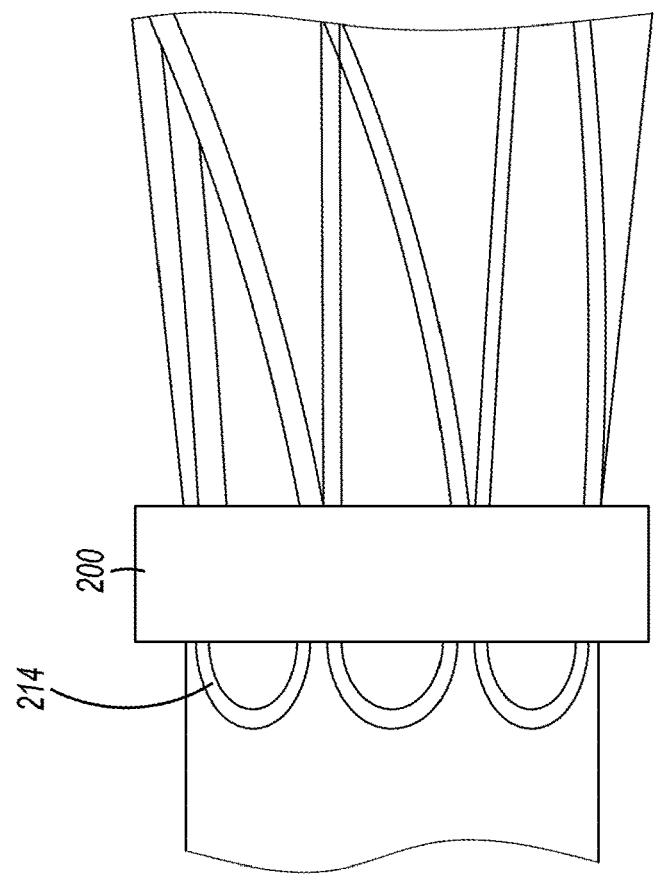
FIG. 5A depicts a perspective view of an exemplary adaptor and FIG. 5B depicts a side view of the exemplary adaptor including wire elements coupled thereto, in accordance with embodiments of the subject matter disclosed herein.
Figure 5A:
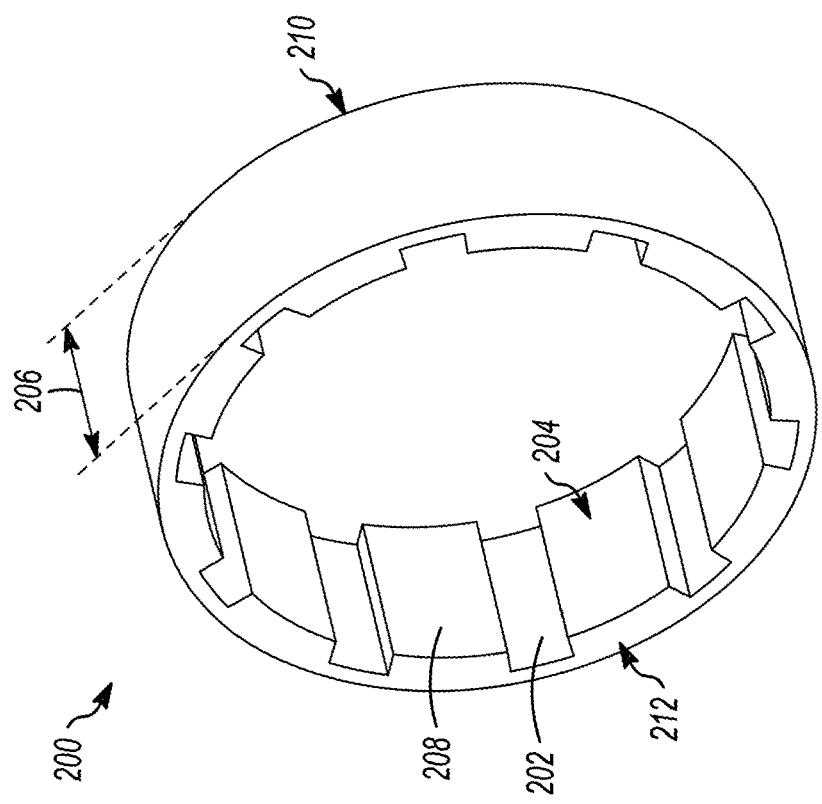

FIG. 5A depicts a perspective view of an exemplary adaptor 200 and FIG. 5B depicts a side view of the exemplary adaptor 200 including wire elements coupled thereto, in accordance with embodiments of the subject matter disclosed herein. Similar to the adaptor 108, the adaptor 200 may secure a cannula (e.g., the cannula 104) to a circulatory support device (e.g., the circulatory support device 102). As illustrated, the adaptor 200 may have a substantially annular cross-sectional profile having an inner diameter through which a circulatory support device may be received. In embodiments, the inner diameter of the adaptor 200 may be configured to receive different sized circulatory support devices. For example, the inner diameter of the adaptor 200 may range from 0.167" to 0.185". In other examples, the inner diameter of the adaptor 200 may be less than 0.167". In even other examples, the inner diameter of the adaptor 200 may be larger than 0.185".

In the illustrated embodiment, the adaptor 200 also includes a plurality of channels 202 circumferentially arranged around an inner surface 204 of the adaptor 200. In embodiments, the channels 202 may extend along an entire length 206 of the adaptor 200. In embodiments, the channels 202 may form posts 208 extending from a distal end 210 of the adaptor 200 to a proximal end 212 of the adaptor 200. For example, a single post 208 may be formed between two channels 202 of the plurality of channels 202. In embodiments, the posts 208 may secure the loop elements of a cannula (e.g., the cannula 104) to the adaptor 200. For example, as illustrated in FIG. 5B, a wire of a cannula may be arranged through a first channel 202 of the plurality of channels 202 around a proximal end 212 of a post 208, and through a second channel 202 of the plurality of channels 202 to form a wire loop 214. Once the adaptor 200 is coupled to a circulatory support device 102, the posts 208 may provide an interference fit with the circulatory support device 102 and prevent the wire loops 214 from pulling out of the adaptor 200.

FIG. 6A depicts a perspective view of another exemplary adaptor 300 and FIG. 6B depicts a side view of the exemplary adaptor 300 including wire elements coupled thereto, in accordance with embodiments of the subject matter disclosed herein. Similar to the adaptor 108, the adaptor 300 may secure a cannula (e.g., the cannula 104) to a circulatory support device (e.g., the circulatory support device 102). As illustrated, the adaptor 300 may have a substantially annular cross-sectional profile having an inner diameter through which a circulatory support device may be received. In embodiments, the inner diameter of the adaptor 300 may be configured to receive different sized circulatory support devices. For example, the inner diameter of the adaptor 300 may range from 0.167" to 0.185". In other examples, the inner diameter of the adaptor 300 may be less than 0.167". In even other examples, the inner diameter of the adaptor 300 may be larger than 0.185".

In embodiments, the adaptor 300 may include a distal cylindrical portion 302 and a proximal cylindrical portion 304. In embodiments, the adaptor 300 also may include a plurality of elongated members 306 that extend between the distal cylindrical portion 302 and the proximal cylindrical portion 304. Additionally, or alternatively, conduits 308 extending through a thickness of the adaptor 300 may separate each of the elongate members 306. In embodiments, the distal cylindrical portion 302, the proximal cylindrical portion 304, and the plurality of elongate members 306 may be a monolithic member. Alternatively, the distal cylindrical portion 302, the proximal cylindrical portion 304, and/or the plurality of elongate members 306 may be separate members.

In embodiments, the adaptor 300 includes a plurality of channels 310 circumferentially arranged around an inner surface 312 of the distal cylindrical portion 302, the proximal cylindrical portion 304, or both. In the illustrated embodiment, the channels 310 may extend along: an entire length 314 of the distal cylindrical portion 302 and/or an entire length 316 of the proximal cylindrical portion 304.

Referring to FIG. 6B, the channels 310 and/or the elongated members 306 may prevent the loop elements of a cannula (e.g., the cannula 104) from pulling out of the adaptor 300. For example, a wire of a cannula may be arranged through a first channel 310 of the plurality of channels 310, around an elongate member 306 and through a second channel 310 of the plurality of channels 310 to form wire loops 318. The arrangement of the wire loops 318 around the elongate members 306 may prevent the wire loops 318 from pulling out of the adaptor 300.

FIG. 7A depicts a perspective view of even another exemplary adaptor 400 and FIG. 7B depicts a side view of the exemplary adaptor 400 including wire loops, in accordance with embodiments of the subject matter disclosed herein. Similar to the adaptor 108, the adaptor 400 may secure a cannula (e.g., the cannula 104) to a circulatory support device (e.g., the circulatory support device 102). As illustrated, the adaptor 400 may have a substantially annular cross-sectional profile having an inner diameter through which a circulatory support device may be received. In embodiments, the inner diameter of the adaptor 400 may be configured to receive different sized circulatory support devices. For example, the inner diameter of the adaptor 400 may range from 0.167" to 0.185". In other examples, the inner diameter of the adaptor 400 may be less than 0.167". In even other examples, the inner diameter of the adaptor 400 may be larger than 0.185".

In embodiments, the adaptor 400 may include a distal cylindrical portion 402 and a proximal cylindrical portion 404. In embodiments, the adaptor 400 also may include a plurality of elongated members 406 that extend between the distal cylindrical portion 402 and the proximal cylindrical portion 404. Additionally, or alternatively, conduits 408 extending through a thickness of the adaptor 400 may separate each of the elongate members 406. In embodiments, the distal cylindrical portion 402, the proximal cylindrical portion 404, and the plurality of elongate members 406 may be a monolithic member. Alternatively, the distal cylindrical portion 402, the proximal cylindrical portion 404, and/or the plurality of elongate members 406 may be separate members.

In embodiments, the adaptor 400 includes a plurality of channels 410 circumferentially arranged around an inner surface 412 of the distal cylindrical portion 402, the proximal cylindrical portion 404, or both. In the illustrated embodiment, the channels 410 may extend along an entire length 414 of the distal cylindrical portion 402 and/or only a portion of the length 416 of the proximal cylindrical portion 404. By only extending along a portion of the length 416 of the proximal cylindrical portion 404, the proximal cylindrical portion 404 may have a larger diameter located near a proximal end 418 of the adaptor 400. As such, a larger diameter circulatory support device may be received by the adaptor 400 in comparison to an embodiment where the channels 410 extend along an entire length 416 of the proximal cylindrical portion 404. Alternatively, the adaptor 400 may have a smaller cross-sectional profile than if the adaptor 400 includes channels 410 extending along an entire length 416 of the proximal cylindrical portion 404 when the same size circulatory support device is used in both embodiments.

Referring to FIG. 7B, the channels 410 and/or the elongated members 406 may prevent the loop elements of a cannula (e.g., the cannula 104) from pulling out of the adaptor 400. For example, a wire of a cannula may be arranged through a first channel 410 of the plurality of channels 410, around an elongate member 406 and through a second channel 410 of the plurality of channels 410 to form wire loops 420. The arrangement of the wire loops 420 around the elongate members 406 may prevent the wire loops 420 from pulling out of the adaptor 400.

Figure 8:
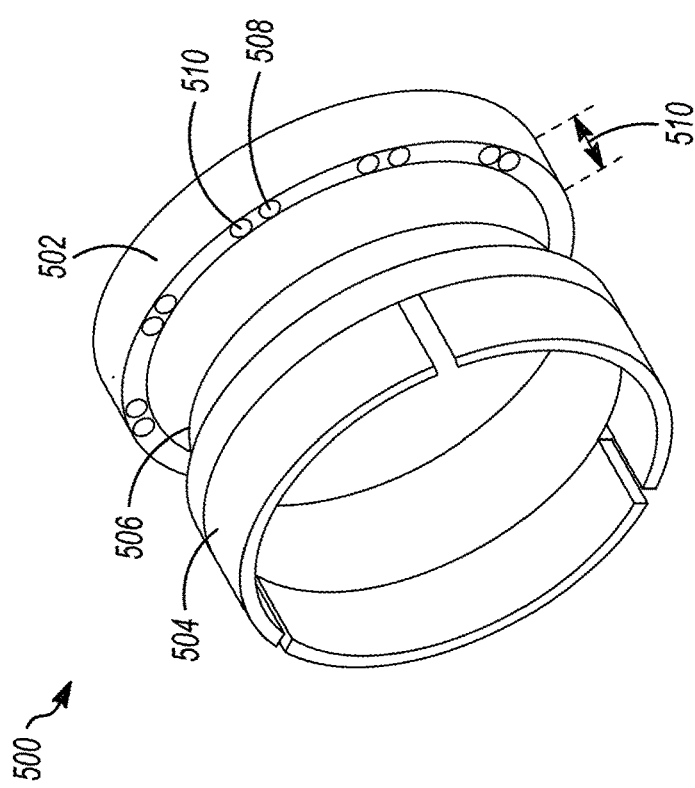
FIG. 8 depicts a perspective view of even another exemplary adaptor, in accordance with embodiments of the subject matter disclosed herein.

FIG. 8 depicts a perspective view of even another exemplary adaptor 500, in accordance with embodiments of the subject matter disclosed herein. Similar to the adaptor 108, the adaptor 500 may secure a cannula (e.g., the cannula 104) to a circulatory support device (e.g., the circulatory support device 102). As illustrated, the adaptor 500 may have a substantially annular cross-sectional profile having an inner diameter through which a circulatory support device may be received. In embodiments, the inner diameter of the adaptor 500 may be configured to receive different sized circulatory support devices. For example, the inner diameter of the adaptor 500 may range from 0.167" to 0.185". In other examples, the inner diameter of the adaptor 500 may be less than 0.167". In even other examples, the inner diameter of the adaptor 500 may be larger than 0.185".

In embodiments, the adaptor 500 may include a distal cylindrical portion 502 and a proximal cylindrical portion 504. In embodiments, the adaptor 500 also may include one or more intermediate cylindrical portions 506 that extend between the distal cylindrical portion 502 and the proximal cylindrical portion 504. In embodiments, the distal cylindrical portion 502, the proximal cylindrical portion 504, and the one or more intermediate cylindrical portions 506 may be a monolithic member. Alternatively, the distal cylindrical portion 502, the proximal cylindrical portion 504, and/or the one or more intermediate cylindrical portions 506 may be separate members.

In embodiments, the adaptor 500 includes a plurality of channels 508 circumferentially arranged around the distal cylindrical portion 502. In the illustrated embodiment, the channels 508 may extend along an entire length 510 of the distal cylindrical portion 502. In embodiments, a wire of a cannula may be arranged through a first channel 508 of the plurality of channels 508, around a proximal end 512 of the distal cylindrical portion 502 and through a second channel 508 of the plurality of channels 508 to form wire loops that are prevented from pulling out of the adaptor 500.

Figure 9:
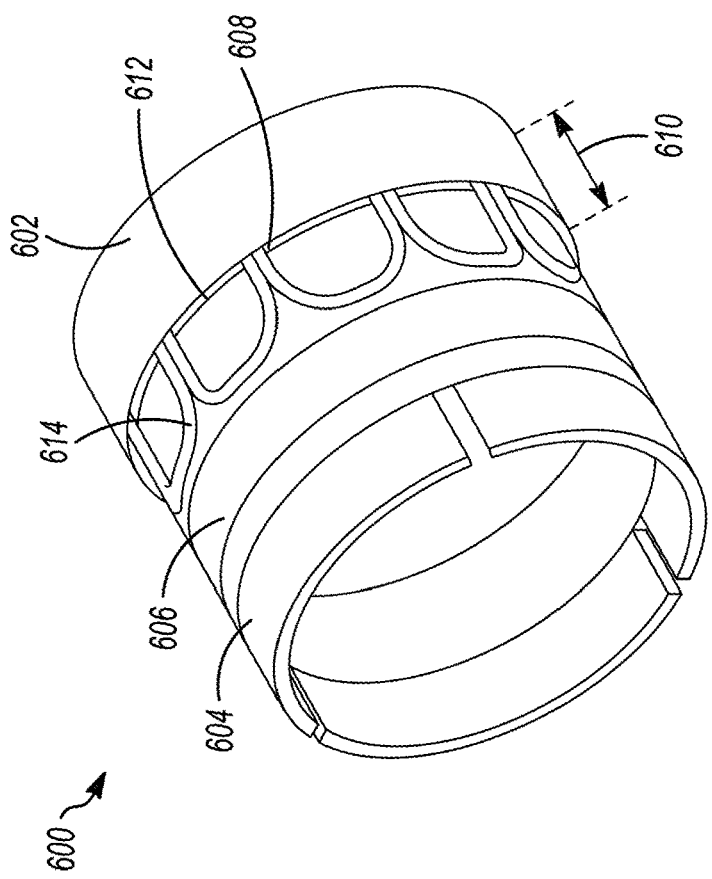
FIG. 9 depicts another perspective view of the exemplary adaptor including wire loops, in accordance with embodiments of the subject matter disclosed herein.

FIG. 9 depicts a perspective view of even another exemplary adaptor 600, in accordance with embodiments of the subject matter disclosed herein. Similar to the adaptor 108, the adaptor 600 may secure a cannula (e.g., the cannula 104) to a circulatory support device (e.g., the circulatory support device 102). As illustrated, the adaptor 600 may have a substantially annular cross-sectional profile having an inner diameter through which a circulatory support device may be received. In embodiments, the inner diameter of the adaptor 600 may be configured to receive different sized circulatory support devices. For example, the inner diameter of the adaptor 600 may range from 0.167" to 0.185". In other examples, the inner diameter of the adaptor 600 may be less than 0.167". In even other examples, the inner diameter of the adaptor 600 may be larger than 0.185".

In embodiments, the adaptor 600 may include a distal cylindrical portion 602 and a proximal cylindrical portion 604. In embodiments, the adaptor 600 also may include one or more intermediate cylindrical portions 606 that extend between the distal cylindrical portion 602 and the proximal cylindrical portion 604. In embodiments, the distal cylindrical portion 602, the proximal cylindrical portion 604, and the one or more intermediate cylindrical portions 606 may be a monolithic member. Alternatively, the distal cylindrical portion 602, the proximal cylindrical portion 604, and/or the one or more intermediate cylindrical portions 606 may be separate members.

In embodiments, the adaptor 600 includes a plurality of channels 608 circumferentially arranged around the distal cylindrical portion 602. In the illustrated embodiment, the channels 608 may extend along an entire length 610 of the distal cylindrical portion 602. In embodiments, a wire of a cannula may be arranged through a first channel 608 of the plurality of channels 608, around a proximal end 612 of the distal cylindrical portion 602 and through a second channel 608 of the plurality of channels 608 to form wire loops 614 that are prevented from pulling out of the adaptor 500. In embodiments, the wire loops 614 may lay in troughs (beneath the wire loops 614) to prevent lateral movement of the wire loops 614.

Figure 10:
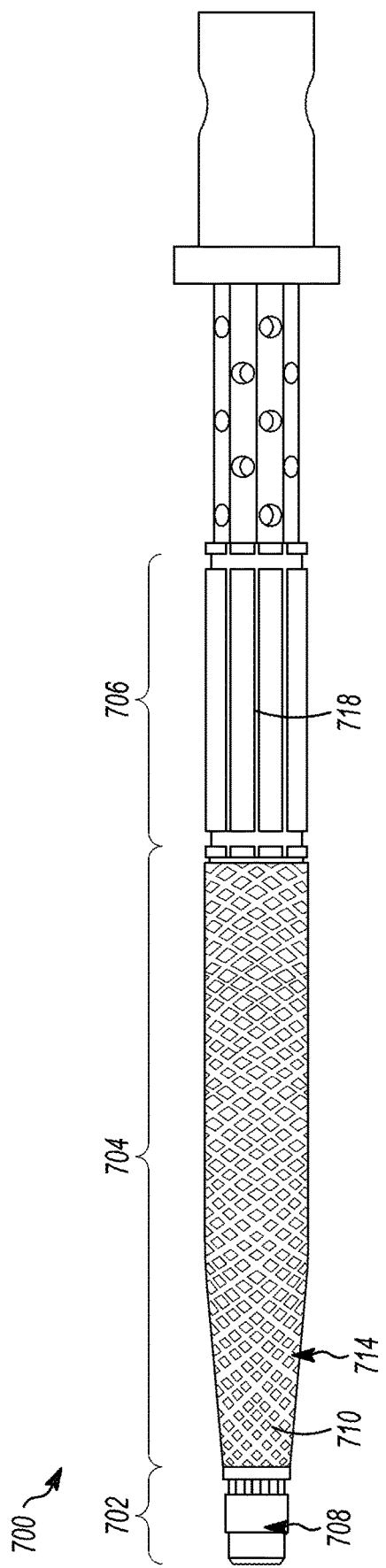
FIG. 10 depicts is a side view of an exemplary mandrel used to form an exemplary cannula, in accordance with embodiments of the subject matter disclosed herein.
Figure 11:
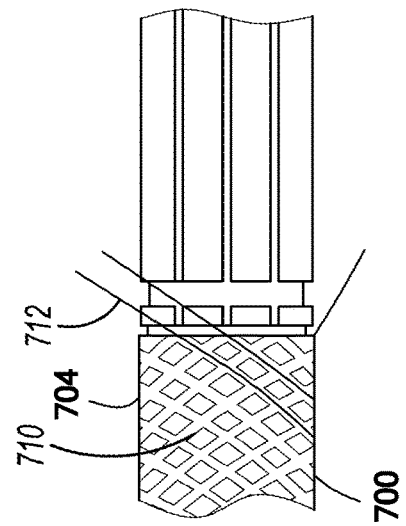
FIG. 11 depicts a side view of a distal portion of the exemplary mandrel depicted in FIG.10, in accordance with embodiments of the subject matter disclosed herein.

FIG. 10 depicts is a side view of an exemplary mandrel 700 used to form an exemplary cannula, in accordance with embodiments of the subject matter disclosed herein. As illustrated, the mandrel 700 comprises a proximal portion 702 including an adaptor 708 coupled thereto, an intermediate portion 704, and a distal portion 706. Proximal portions of wires 712 (shown in FIG. 11) may be arranged through channels in the adaptor 708 to keep the wires 712 stationary while the braiding of the wires 712 is performed. In embodiments, the mandrel 700 also includes a plurality of protrusions 710. As illustrated in FIG. 11, which depicts a side view of a distal portion of the exemplary mandrel depicted 700 in FIG.10, wires 712 may be wrapped and/or braided around the plurality of protrusions 710 to form the braided mesh (e.g., the braided mesh 124) of the cannula (e.g., the cannula 104). In embodiments, the intermediate portion 704 may include protrusions 710 having a constant pitch or a varying pitch.

Figure 14B:
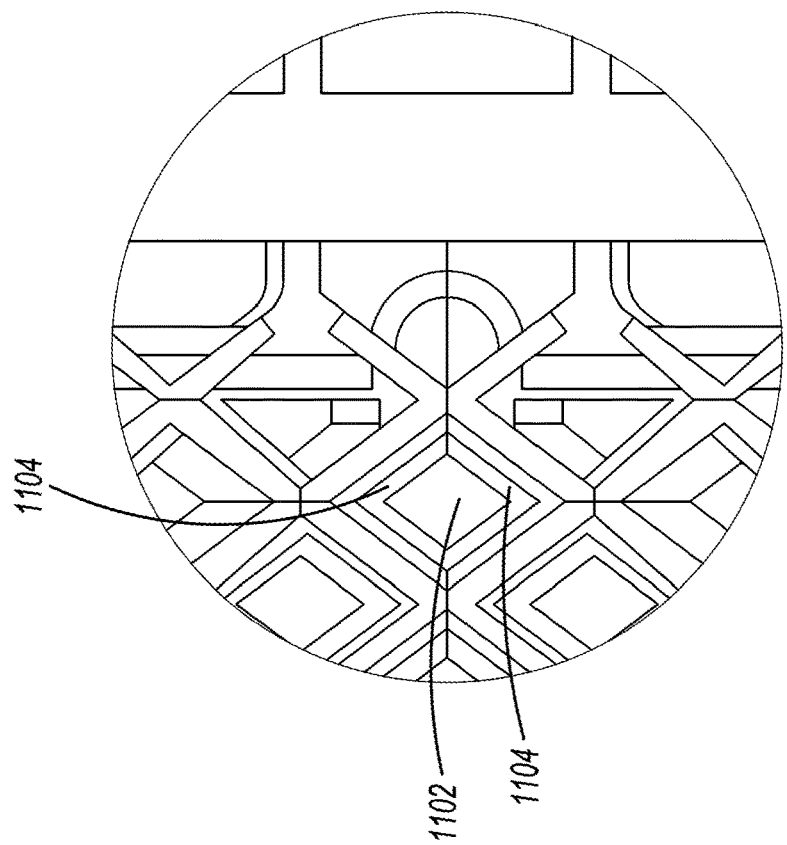
FIGS. 14A-14B depict different pitches used in an exemplary mandrel, in accordance with embodiments of the subject matter disclosed herein.
Figure 14A:
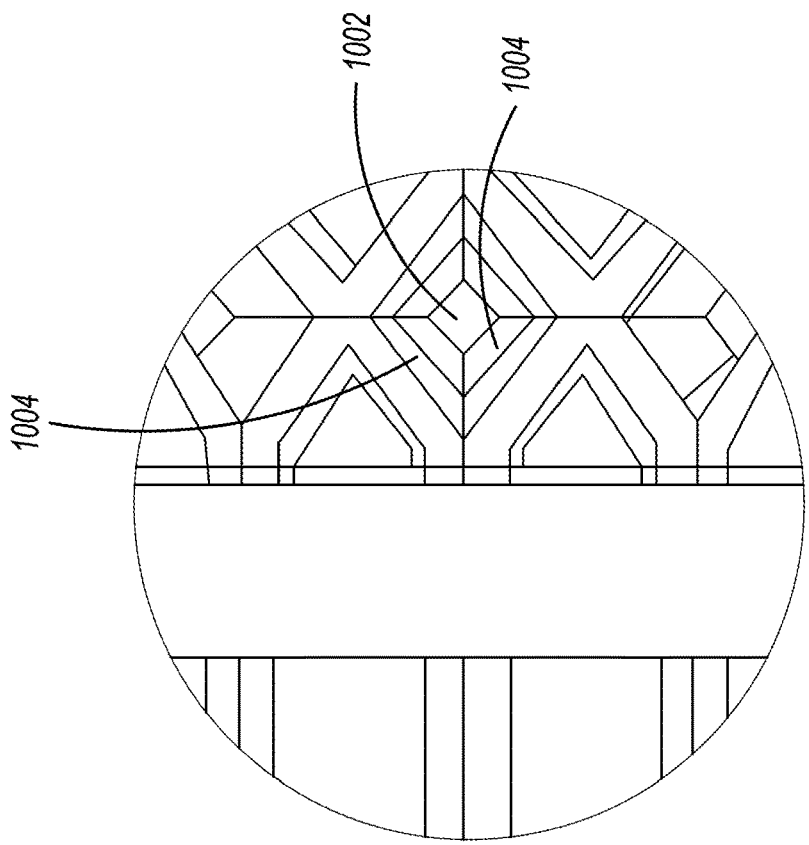

FIG. 12 illustrates an exemplary mandrel 800 including protrusions 802 having a constant pitch and FIG. 13 illustrates an exemplary mandrel 900 including protrusions 902 having a varying pitch. In embodiments, a pitch angle is the angle formed by two proximal edges of a protrusion and/or two distal edges of a protrusion. For example, referring to FIGS. 14A-14B, two different pitch angles are illustrated. In FIG. 14A, the protrusion 1002 has edges 1004 that form a pitch angle of 78 degrees. In comparison, the protrusion 1102 has edges 1104 that form a pitch angle of 110 degrees. However, these are only examples and not meant to be limiting and the pitch angle may range from approximately 30 degrees to 150 degrees.

In embodiments, the pitch angle may determine the dimetric and/or the axial strength of the cannula (e.g., the cannula 104). For example, a greater pitch angle may facilitate a greater dimetric strength while also facilitating a lower axial strength. In comparison, the smaller pitch angle may facilitate a lower dimetric strength while also facilitating a greater axial strength. In embodiments, the dimetric strength and/or the axial strength may be configured for the specific application of cannula and/or selected to withstand the pressure gradient between the inside and the outside of the cannula.

Referring back to FIG. 10, the intermediate portion 704 may include a tapered portion 714 which can be used to form a tapered proximal portion (e.g., the tapered proximal portion 126) of a cannula.

In embodiments, once the wires 712 are braided through the protrusions 710 to a distal end 716 of the protrusions 710, every other wire 712 may be looped back and arranged back through the protrusions 710. The wires 712 that are not looped back may be arranged through conduits 718 of the distal portion 706. In embodiments, once the shape of the wires 712 is formed, the looped back portions of the wires 712 or the entirety of the wires 712 may be welded, affixed, stabilized, and/or heat threated to set the shape of the wires 712. The cannula may then be removed from the mandrel 700. After removing the cannula from the mandrel 700, the cannula may be coated in a membrane.

Figure 15:
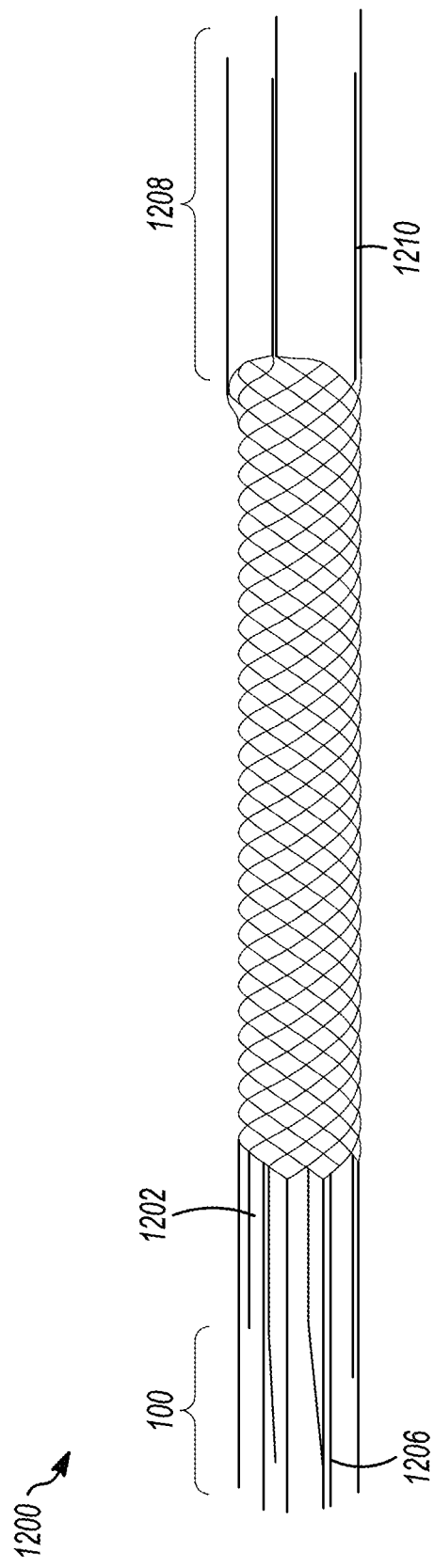
FIG. 15 depicts a side view of an exemplary cannula having a membrane coating, in accordance with embodiments of the subject matter disclosed herein.

FIG. 15 depicts a side view of an exemplary cannula 1200 that was removed from a mandrel (e.g., the mandrel 700) and has a membrane coating 1202, in accordance with embodiments of the subject matter disclosed herein. In embodiments, the membrane may be silicone. As illustrated, the proximal portion 1204 includes a plurality of proximal wire portions 1206 extending in a proximal direction. In at least some embodiments, the proximal wire portions 1206 may extend longitudinally. These wires 1206 may be looped through an adaptor (e.g., any one of the adaptors 108, 200, 300, 400, 500, 600 discussed above) and then secured to a circulatory support device, as described above. In embodiments, the distal portion 1208 includes a plurality of distal wire portions 1210 extending in a distal direction. In at least some embodiments, the distal wire portions 1210 extend longitudinally. These wires 1210 may be coupled to a tip element (e.g., the tip element 136 discussed above), as discussed above.

Various modifications and additions can be made to the exemplary embodiments discussed without departing from the scope of the present disclosure. For example, while the embodiments described above refer to particular features, the scope of this disclosure also includes embodiments having different combinations of features and embodiments that do not include all of the described features. Accordingly, the scope of the present disclosure is intended to embrace all such alternatives, modifications, and variations as fall within the scope of the claims, together with all equivalents thereof.

What is claimed is:

1. An apparatus for attachment to a cardiac pump, the apparatus comprising:
   an adaptor comprising:
      an annular cross section configured to receive the cardiac pump, wherein the annular cross section is secured to the cardiac pump; and
      a plurality of channels arranged around the adaptor, the plurality of channels extending along an entire length of the adaptor;
   a cannula comprising a proximal portion, a distal portion, and an intermediate portion comprising a braided mesh extending between the distal portion and the proximal portion, the proximal portion having a proximal end comprising a plurality of elements arranged through the channels and the distal portion comprising a plurality of wires and a tip element, wherein the plurality of wires extend in a distal direction from the braided mesh to the tip element, wherein the plurality of wires are secured to the tip element; and
   a coating covering at least a portion of the braided mesh.

2. The apparatus of claim 1, wherein the adaptor comprises a distal cylindrical portion, a proximal cylindrical portion, and a plurality of elongate members extending from the distal cylindrical portion to the proximal cylindrical portion, wherein conduits extending through a thickness of the adaptor separate each of the elongate members.

3. The apparatus of claim 2, wherein the elongate members extend along an interior surface of the distal cylindrical portion, the proximal cylindrical portion, or both.

4. The apparatus of claim 3, wherein the elongate members extend along an entire length of the distal cylindrical portion, the proximal cylindrical portion, or both.

5. The apparatus of claim 1, wherein a proximal portion of the braided mesh comprises a tapered portion that increases in diameter from a proximal end of the tapered portion to a distal end of the tapered portion.

6. The apparatus of claim 1, wherein the braided mesh comprises a constant pitch.

7. The apparatus of claim 1, wherein the braided mesh comprises a varying pitch.

8. The apparatus of claim 1, wherein the channels extend along an interior surface of the adaptor.

9. The apparatus of claim 1, wherein at least one of the plurality of channels extends longitudinally.

10. The apparatus of claim 1, wherein the adaptor comprises a distal cylindrical portion, a proximal cylindrical portion, and one or more intermediate cylindrical portions extending between the distal cylindrical portion and the proximal cylindrical portion, wherein the intermediate cylindrical portion has a smaller diameter than the distal cylindrical portion, and wherein the channels extend through a length of the distal cylindrical portion.

11. The apparatus of claim 1, wherein the plurality of elements are a plurality of loop elements.

12. The apparatus of claim 1, wherein the entire length of the adaptor extends from a proximal side to a distal side of the adaptor.

13. The apparatus of claim 1, wherein an interior surface of the adaptor includes a plurality of posts, and each channel of the plurality of channels is disposed between adjacent posts of the plurality of posts.

14. An apparatus for attachment to a cardiac pump, the apparatus comprising:
   an adaptor including a longitudinal direction extending from a proximal side to a distal side of the adaptor, the adaptor comprising:
      an annular cross section configured to receive the cardiac pump, wherein the annular cross section is secured to the cardiac pump; and
      a plurality of channels arranged around the adaptor, wherein at least one of the plurality of channels extends in the longitudinal direction;
   a cannula comprising a proximal portion, a distal portion, and an intermediate portion comprising a braided mesh extending between the distal portion and the proximal portion, the proximal portion having a proximal end comprising a plurality of elements arranged through the channels and the distal portion comprising a plurality of wires and a tip element, wherein the plurality of wires extend in a distal direction from the braided mesh to the tip element, wherein the plurality of wires are secured to the tip element; and
   a coating covering at least a portion of the braided mesh.

15. An apparatus for attachment to a cardiac pump, the apparatus comprising:
   an adaptor comprising:
      an annular cross section configured to receive the cardiac pump, wherein the annular cross section is secured to the cardiac pump;
      a plurality of channels arranged around the adaptor;
      a distal cylindrical portion;
      a proximal cylindrical portion; and
      a plurality of elongate members extending from the distal cylindrical portion to the proximal cylindrical portion, wherein conduits extending through a thickness of the adaptor separate each of the plurality of elongate members;
   a cannula comprising a proximal portion, a distal portion, and an intermediate portion comprising a braided mesh extending between the distal portion and the proximal portion, the proximal portion having a proximal end comprising a plurality of elements arranged through the channels and the distal portion comprising a plurality of wires and a tip element, wherein the plurality of wires extend in a distal direction from the braided mesh to the tip element, wherein the plurality of wires are secured to the tip element; and
   a coating covering at least a portion of the braided mesh.

16. The apparatus of claim 15, wherein the distal portion of the cannula is disposed distally relative to the distal cylindrical portion of the adaptor.

\* \* \* \* \*